United States Patent
Stevenson et al.

(10) Patent No.: US 7,806,842 B2
(45) Date of Patent: Oct. 5, 2010

(54) CABLE-BASED ORTHOPEDIC BRACING SYSTEM

(75) Inventors: Craig G. Stevenson, Logan, UT (US); Jarvis K. Parry, Providence, UT (US)

(73) Assignee: SP Design, LLC, Logan, UT (US)

( * ) Notice: Subject to any disclaimer, the term of this patent is extended or adjusted under 35 U.S.C. 154(b) by 148 days.

(21) Appl. No.: 11/697,685

(22) Filed: Apr. 6, 2007

(65) Prior Publication Data
US 2008/0249448 A1 Oct. 9, 2008

(51) Int. Cl.
*A61F 5/00* (2006.01)
(52) U.S. Cl. .................. 602/26; 602/5; 602/16
(58) Field of Classification Search ......... 602/5, 602/16, 20, 23, 26, 60–62; 128/882
See application file for complete search history.

(56) References Cited

U.S. PATENT DOCUMENTS

| | | | |
|---|---|---|---|
| 3,802,438 A | 4/1974 | Wolvek | |
| 4,128,921 A | 12/1978 | Heinze et al. | |
| 5,423,820 A | 6/1995 | Miller et al. | |
| 5,575,764 A | 11/1996 | Van Dyne | |
| 5,599,288 A | 2/1997 | Shirley et al. | |
| 5,720,747 A | 2/1998 | Burke | |
| 5,772,618 A | 6/1998 | Mason et al. | |
| 5,782,780 A | 7/1998 | Mason et al. | |
| 5,807,294 A | 9/1998 | Cawley et al. | |
| 5,857,988 A | 1/1999 | Shirley | |
| 5,934,599 A | 8/1999 | Hammerslag | |
| 6,110,138 A | 8/2000 | Shirley | |
| 6,202,953 B1 | 3/2001 | Hammerslag | |
| 6,289,558 B1 | 9/2001 | Hammerslag | |
| 6,517,502 B2 | 2/2003 | Heyman et al. | |
| 6,602,214 B2 | 8/2003 | Heinz et al. | |
| 6,719,713 B2 | 4/2004 | Mason | |
| 6,964,644 B1 | 11/2005 | Garth | |
| 7,001,348 B2 | 2/2006 | Garth et al. | |
| 2002/0032397 A1* | 3/2002 | Coligado | 602/5 |
| 2002/0068890 A1* | 6/2002 | Schwenn et al. | 602/19 |
| 2003/0171703 A1 | 9/2003 | Grim et al. | |
| 2003/0208146 A1 | 11/2003 | Kania | |
| 2006/0020237 A1* | 1/2006 | Nordt et al. | 602/60 |
| 2006/0156517 A1 | 7/2006 | Hammerslag et al. | |

(Continued)

OTHER PUBLICATIONS

Tagg Industries, Isodyn Knee Brace, www.taggindustries.com, available, on information and belief, at least as early as Feb. 16, 2004, 2 pages.

(Continued)

*Primary Examiner*—Patricia M Bianco
*Assistant Examiner*—Keri J Nicholson
(74) *Attorney, Agent, or Firm*—Workman Nydegger

(57) ABSTRACT

An orthopedic bracing system for providing support to a joint of an individual is provided. The bracing system includes a frame configured to conform to the individual's body and configured to contact the individual such that it can provide support to the joint. The frame has at least two portions configured to connect at least a first part of the individual's body to a second part of the individual's body. The bracing system further includes a cable interconnected to the frame, and an adjustment mechanism for adjusting the tightness level of the cable.

36 Claims, 10 Drawing Sheets

U.S. PATENT DOCUMENTS

| | | |
|---|---|---|
| 2006/0167394 A1 | 7/2006 | Ceriani et al. |
| 2007/0169378 A1 | 7/2007 | Sodeberg et al. |
| 2008/0066272 A1 | 3/2008 | Hammerslag et al. |

OTHER PUBLICATIONS

Bellacure, Restore Your Lifestyle, www.bellacure.com, available, on information and belief, at least as early as Feb. 7, 2006, copyright 2005, 6 pages.

"Bellacure: The Treatment Device," www.bellacure.com/en/products/, printed Dec. 14, 2007, copyright 2005, 5 color pages.

DC Snow "Allegiance," http://www.dcshoecousa.com/snow/; printed on Apr. 5, 2007 (5 pages).

International Search Report and Written Opinion from PCT/US 08/59484 dated Sep. 4, 2008.

U.S. Appl. No. 60/843,830, filed Sep. 12, 2006, Hammerslag et al.

Breg, photographs of knee brace, available, on information and belief, at least as early as Dec. 31, 2005, 5 pages.

Pictures of snow board boot, which was available, on information and belief, at least as early as Sep. 2006 (11 pictures, 3 pages).

Printouts from www.dcshoecousa.com/snow/; dated Apr. 3, 2007 (4 pages).

\* cited by examiner

CABLE-BASED ORTHOPEDIC BRACING SYSTEM

BACKGROUND OF THE INVENTION

1. The Field of the Invention

This invention generally relates to orthopedic devices.

2. The Relevant Technology

Today, orthopedic devices such as functional knee braces are commonplace for use as a substitute for damaged ligaments or for use to prevent injury or to prevent further injury. Often, braces are prescribed following surgery to prevent further injury at that critical time for healing. In the area of the knee, typical injuries include the anterior cruciate ligament (ACL) injury, medial collateral ligament (MCL) injuries, and injuries to the posterior cruciate ligament (PCL). All of these injuries involve damage to ligaments that are important to stability of the knee joint.

FIG. 1 shows a cut-away view surrounding someone's knee 8 and a typical prior art knee brace 10 that is designed to stabilize the knee joint that is already injured or to prevent an injury or further injury. Typical knee brace 10 comprises a rigid frame 12 to provide stability, a soft material such as neoprene to provide the primary body material 14, which has a hole 7 leaving the knee 8 exposed, and straps 16 usually made of fabric hook-and-loop fasteners, such as VELCRO®, to hold everything in place.

A typical prior art orthopedic device such as knee brace 10, however, has many drawbacks. Orthopedic devices are typically worn during activity, and such activity causes perspiration and water vapor that tends to accelerate wear and tear on the soft materials 14 and 16 of the brace 10. Straps 16 tend to have rough edges, particularly if fabric hook-and-loop fasteners, such as VELCRO®, and these rough edges irritate the skin, even if worn over a layer of clothing. Also, straps 16, particularly if fabric hook-and-loop fasteners, such as VELCRO®, wear out quickly, especially if used frequently. In addition, fabric hook-and-loop fasteners, such as VELCRO® straps 16 have a tendency to stick to fleece or mesh, which is often worn as under-layers of clothing.

Further, with many braces, a strap system may surround the entire knee with two or more relatively long straps 16. In such strap systems, the user must undo an entire strap and redo it in order to tighten a brace. During activity, sports and the like, braces often need tightening and muscles swell and contract, so this can be a common occurrence, and thus particularly problematic. Lastly, one may be able to adjust a typical orthopedic device such as the knee brace 10 to a desired tightness for an activity or sport, but then the brace then may be too tight for a rest or break during that activity.

Therefore, there is a great need in the general area of orthopedic braces for a device that solves the above problems. It is, therefore, an object of the present invention to provide an improved orthopedic brace. Specifically, it is an object of the present invention to provide an orthopedic bracing system that is more comfortable, easier to use, simpler to loosen, simpler to tighten, and is longer lasting than existing braces.

BRIEF SUMMARY OF THE INVENTION

An orthopedic bracing system for providing support to a joint of an individual is provided. The bracing system comprises a frame configured to conform to the individual's body and configured to contact the individual such that it can provide support to the joint. The frame has at least two portions configured to connect at least a first part of the individual's body to a second part of the individual's body. The bracing system further comprises a cable interconnected to the frame, and an adjustment mechanism for adjusting the tightness level of the cable.

Typically, the portions of the frame are rigid and are rotatably connected by at least one hinge. In some embodiments, the orthopedic bracing system further comprises body material connected to the frame. In certain embodiments, the adjustment mechanism comprises a ratchet. In some embodiments, the cable also is interconnected to the body material in addition to the frame. In many embodiments, the orthopedic bracing system further comprises eyelets affixed to the frame for guiding the cable about the frame and sharp turns. Several embodiments also comprise a sheath affixed to the body material for guiding the cable about the body material and protecting the body material from wear and tear.

In one embodiment, the orthopedic bracing system comprises a frame and at least one adjustment system, wherein the adjustment system comprises a cable interconnected to the frame, an adjustment mechanism for adjusting the tightness level of the cable, and a first strap interconnected to the frame by means of at least one anchor pin, wherein the at least one anchor pin is movably connected to the frame. In certain of these embodiments, the at least first strap is flexible. The bracing system further comprises at least one anchor clip that houses the at least one anchor pin. The adjustment system further comprises two anchor clips, wherein the first strap is affixed to and between the at least two anchor clips. In some embodiments, the adjustment system has a second strap affixed to and between two anchor clips that do not use anchor pins. In yet additional embodiments, the frame is customized to fit the body parts of a particular individual.

BRIEF DESCRIPTION OF THE DRAWINGS

In order that the manner in which the above-recited and other advantages and objects of the invention are obtained, a more particular description of the invention briefly described above will follow by reference to specific embodiments thereof that are illustrated in the appended drawings. These drawings depict only typical embodiments of the invention. They are not, therefore, to be considered to be limiting of its scope. The invention will be described and explained with additional specificity and detail through the use of the accompanying drawings in which.

DETAILED DESCRIPTION OF THE PREFERRED EMBODIMENTS

The following detailed description of exemplary embodiments of the invention makes reference to the accompanying drawings, which show, by way of illustration, exemplary embodiments in which the invention may be practiced. While these exemplary embodiments are described in sufficient detail to enable those skilled in the art practice the invention, it should be understood that other embodiments may be realized and that various changes to the invention may be made without departing from the spirit and scope of the present invention. Thus, the following more detailed description of the embodiments of the present invention, as represented in the figures, is not intended to limit the scope of the invention, as claimed. It is presented for purposes of illustration only and to describe the features and characteristics of the present invention, to set forth the best mode of operation of the invention, and to sufficiently enable one skilled in the art to practice the invention. Accordingly, the scope of the present invention is to be defined solely by the appended claims. The following detailed description and exemplary embodiments of the invention will be best understood by reference to the accompanying drawings, wherein the elements and features of the invention are designated by numerals throughout.

The present invention describes and features a cable-based orthopedic bracing system that is more comfortable, easier to use, simpler to loosen and simpler to tighten, and is longer lasting than existing braces.

With reference to the accompanying drawings, advantages of the present invention will be apparent in light of the detailed description set forth below. These advantages are not meant to be limiting in any way. Indeed, other than those specifically recited herein, one skilled in the art will appreciate that other advantages may be realized, upon practicing the present invention.

Figure 2:
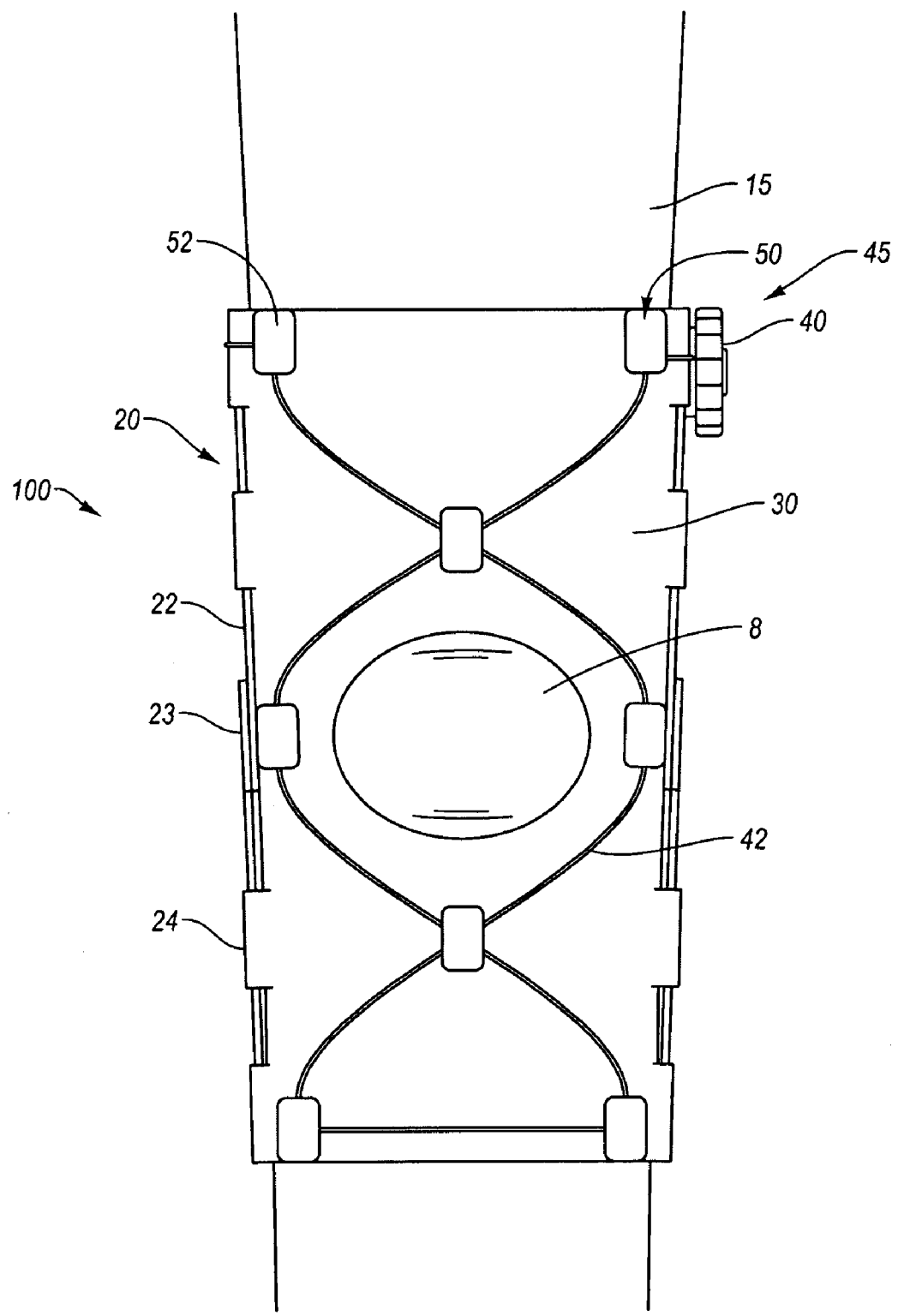
FIG. 2 shows a front view of one embodiment of a cable-based orthopedic bracing system according to the present invention.

FIG. 2 shows a front view of one embodiment of a cable-based orthopedic bracing system 100 according to the present invention. Specifically, FIG. 2 shows a cable-based knee brace 100. As shown, the cable-based knee brace 100 comprises a frame 20, a body material 30, and an adjustment system 45. With the brace 100, the frame 20 has four parts: an upper 22 and lower section 24 on each side of the knee 8, with each upper 22 and lower section 24 being pivotally connected by means of a hinge 23. Further, with brace 100, the body material 30 is flexible and is typically neoprene. Lastly, the adjustment system 45 comprises an adjustment mechanism 40, a cable 42, and a routing system 50, which itself comprises eyelets 52 for guiding the cable 42 around the frame 20. By use of the routing system 50, the cable 42 is interconnected to the frame 40 and body material 30. Note that the cable 42 can be any thin elongated material, such as wire, line, cord, string, or the like.

Thus, the neoprene material 30 gives body to the brace 100 while the frame 20 provides the needed support to the knee 8. Also, the brace 20 is configured to conform to an individual's body and configured to contact the individual, either directly to the skin or through clothing worn by the individual. The brace 100 is placed over the knee 8 as one would put on a sock and then one adjusts the fit or tightness level with the aid of the adjustment system 45. The adjustment system 45 is merely a ratchet type system for use with a small diameter cable. Such a system is known to one skilled in the art and is disclosed, e.g., in U.S. Pat. No. 5,934,599, which is hereby incorporated in its entirety by reference.

As shown in FIG. 2, the cable 42 extends from the adjustment mechanism 40 uniformly about the frame 20 and by means of and through the eyelets 52 and back to the adjustment mechanism 40. As the cable is tightened by the adjustment mechanism 40, e.g., by turning, it is pulled there and thereby pulled at each eyelet 52, thereby uniformly tightening the brace 100 to ensure a uniform, snug and proper fit around the user's knee 8. To loosen, the user need only loosen the ratchet system, i.e., the adjustment mechanism 40, which thereby loosens the tension at each eyelet 52 location about the brace 100.

Figure 1:
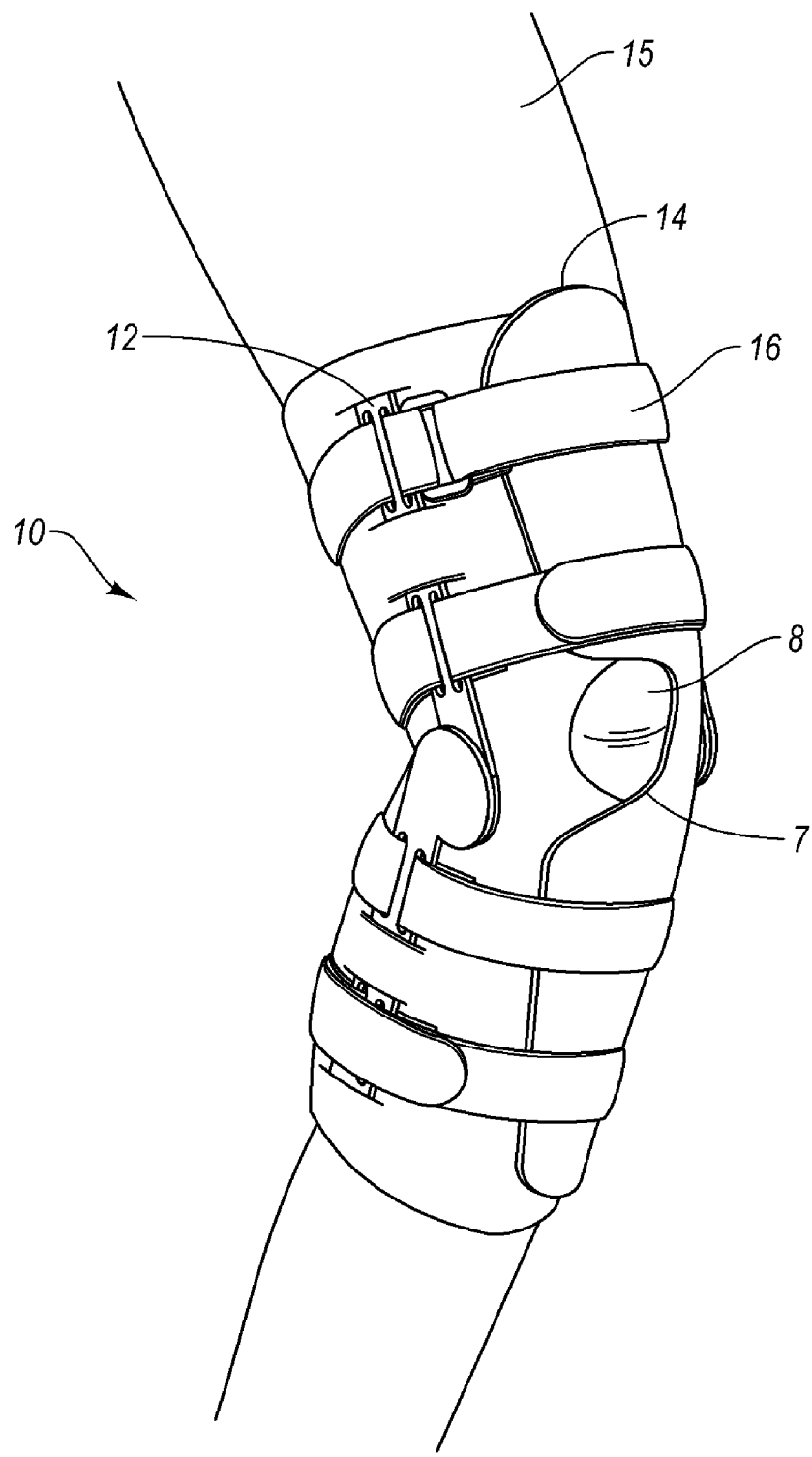
FIG. 1 shows front view of a prior art knee brace.

Re-tightening can be achieved and re-loosening can be achieved in the same manner as it was originally performed. In this way, the cable-based knee brace 100 of the present invention is more comfortable, easier to use, simpler to loosen, simpler to tighten, and is longer lasting than conventional knee braces. See, e.g. the conventional knee brace 10 of FIG. 1. For example, when one's muscles swell or contract or when one takes a rest during activity and they need adjustment on one's knee brace, the process is much easier, simpler and endures much less wear and tear on the brace 100 than it would on a conventional knee brace. Also, the desired fit and tightness achieved with the cable-based knee brace 100 is much more snug than with a conventional knee brace. More importantly, however, the knee brace 100 can be tightened more easily and more readily and more uniformly than can be achieved with a conventional knee brace.

Figure 2A:
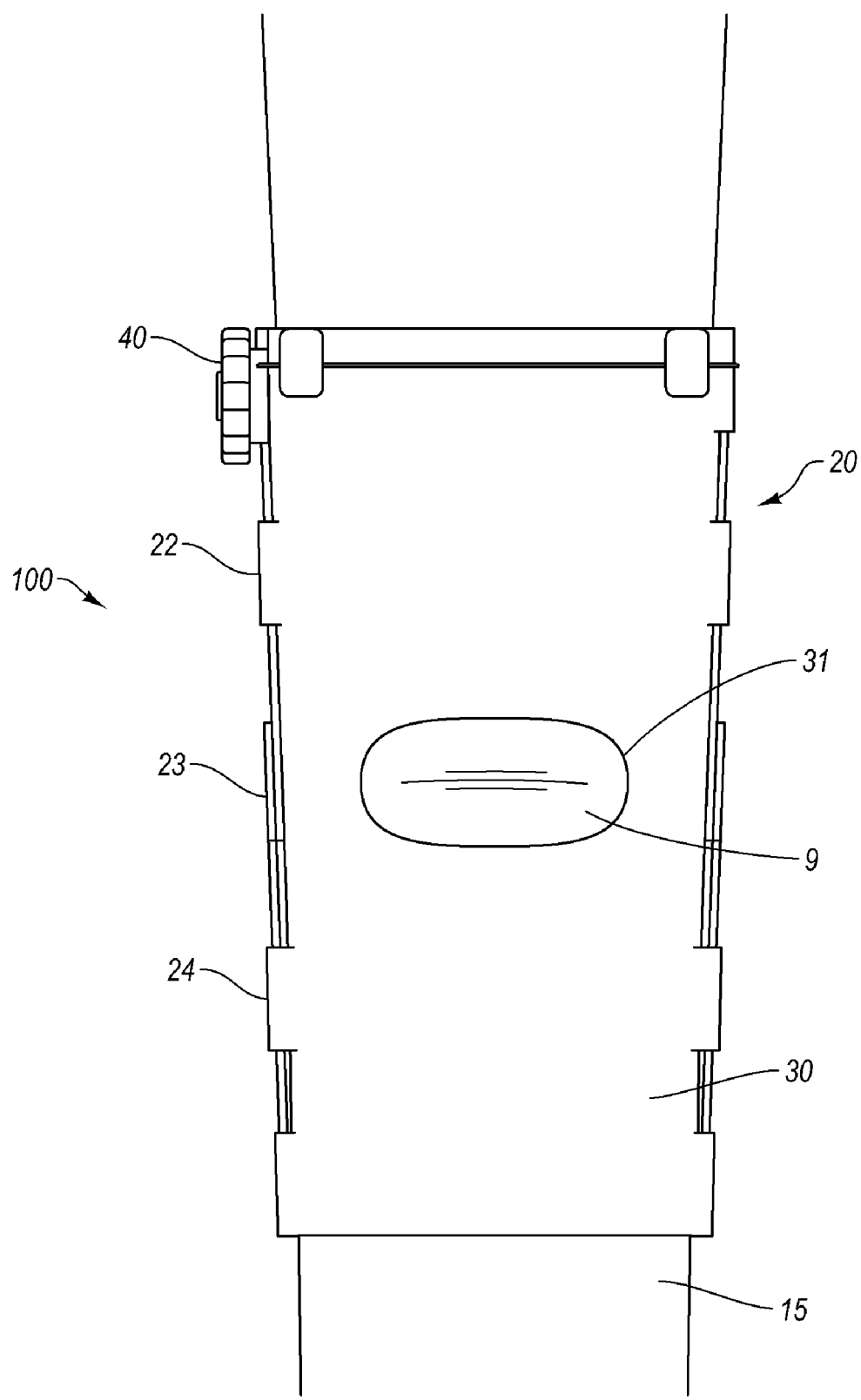
FIG. 2A shows a rear view of the cable-based orthopedic bracing system of FIG. 2.

FIG. 2A shows a rear view of the cable-based orthopedic bracing system 100 of FIG. 2. As shown in FIG. 2A, portions 22 and 24 of the frame 20 (including hinge 23) are visible from the rear, as well as the adjustment mechanism 40, all of which are positioned on the side of the brace 100. As the brace 100 is placed over the knee 8 as one would put on a sock, the rear of the brace 100 is comprised of body material 30 and has a hole 31 to accommodate the area 9 behind the knee 8.

Figure 2B:
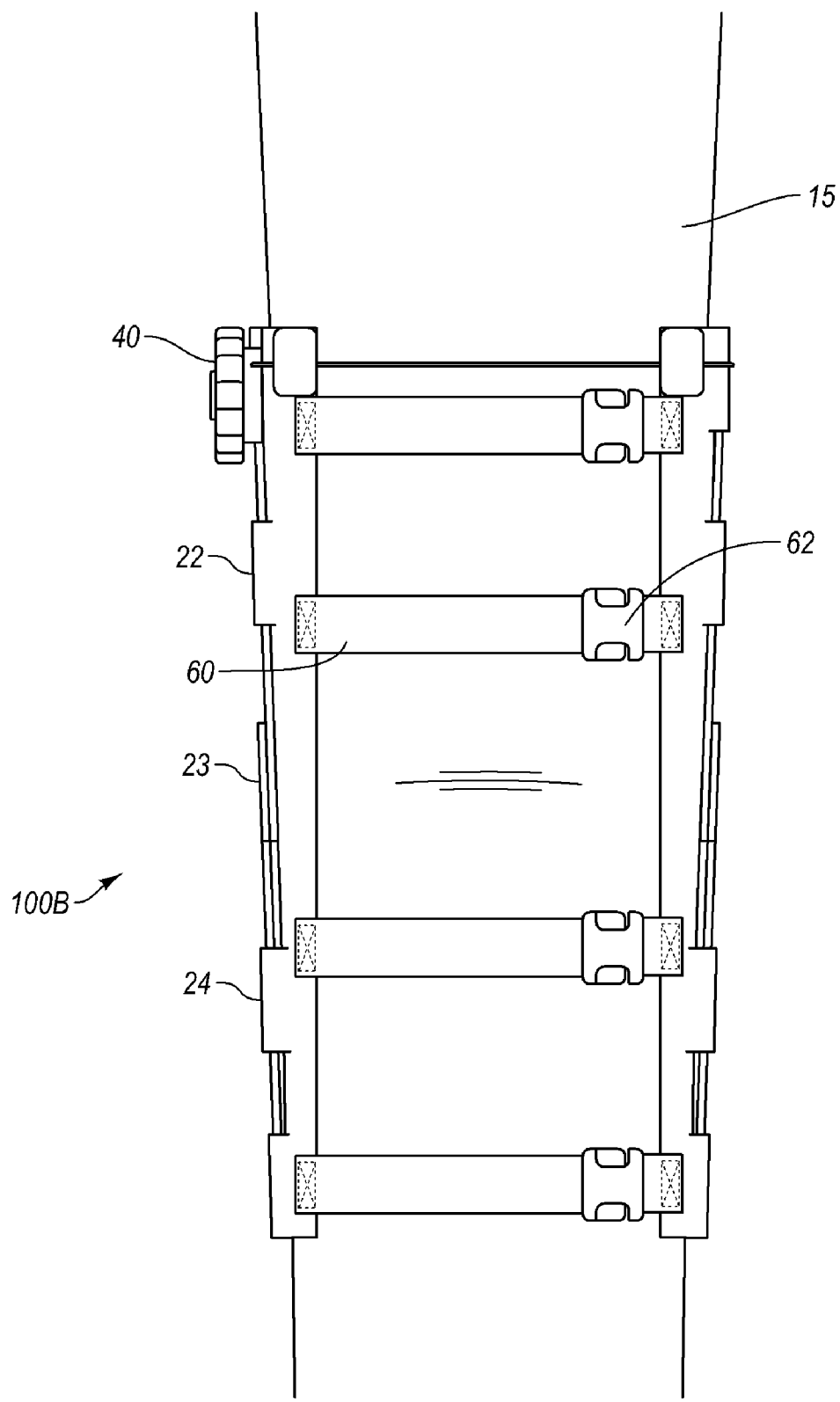
FIG. 2B shows a rear view of an alternate embodiment of a cable-based orthopedic bracing system.

FIG. 2B shows a rear view of an alternate embodiment of a cable-based orthopedic bracing system 100B. The bracing system 100B has the same front as the bracing system 100 of FIG. 2, but has a different rear design, i.e., that shown in FIG. 2B. As shown in FIG. 2B, portions 22 and 24 of the frame 20 (including hinge 23) are visible from the rear, as well as the adjustment mechanism 40, all of which are positioned on the side of the brace 100B. Instead of being placed over the knee 8 as one would put on a sock, however, the rear of brace 100B comprises of four straps 60 that extend between side portions 22 and 24 of the frame 20, respectively. As shown in FIG. 2B, each strap 60 attaches to the other side of the frame 20 by means of a clip 62. As shown, the straps 60 and clips 62 are conventional straps and clips, but any mechanism that can connect the respective portions 22 and 24 of the frame 20 across the open space of the leg 15 is contemplated. Further, some flexibility in the straps 60 is allowable, but the primary mechanism for adjusting the fit of the brace in either bracing system 100 or 100B is provided by the adjustment system 45 positioned on the front of the brace, as shown in FIG. 2. In the embodiment of bracing system 100B, the rear of brace 100B has no body material 30 like brace 100, but may contain some material to make the interaction between skin on the leg 15 and the straps 60 as comfortable as possible.

Figures 3, 3A:
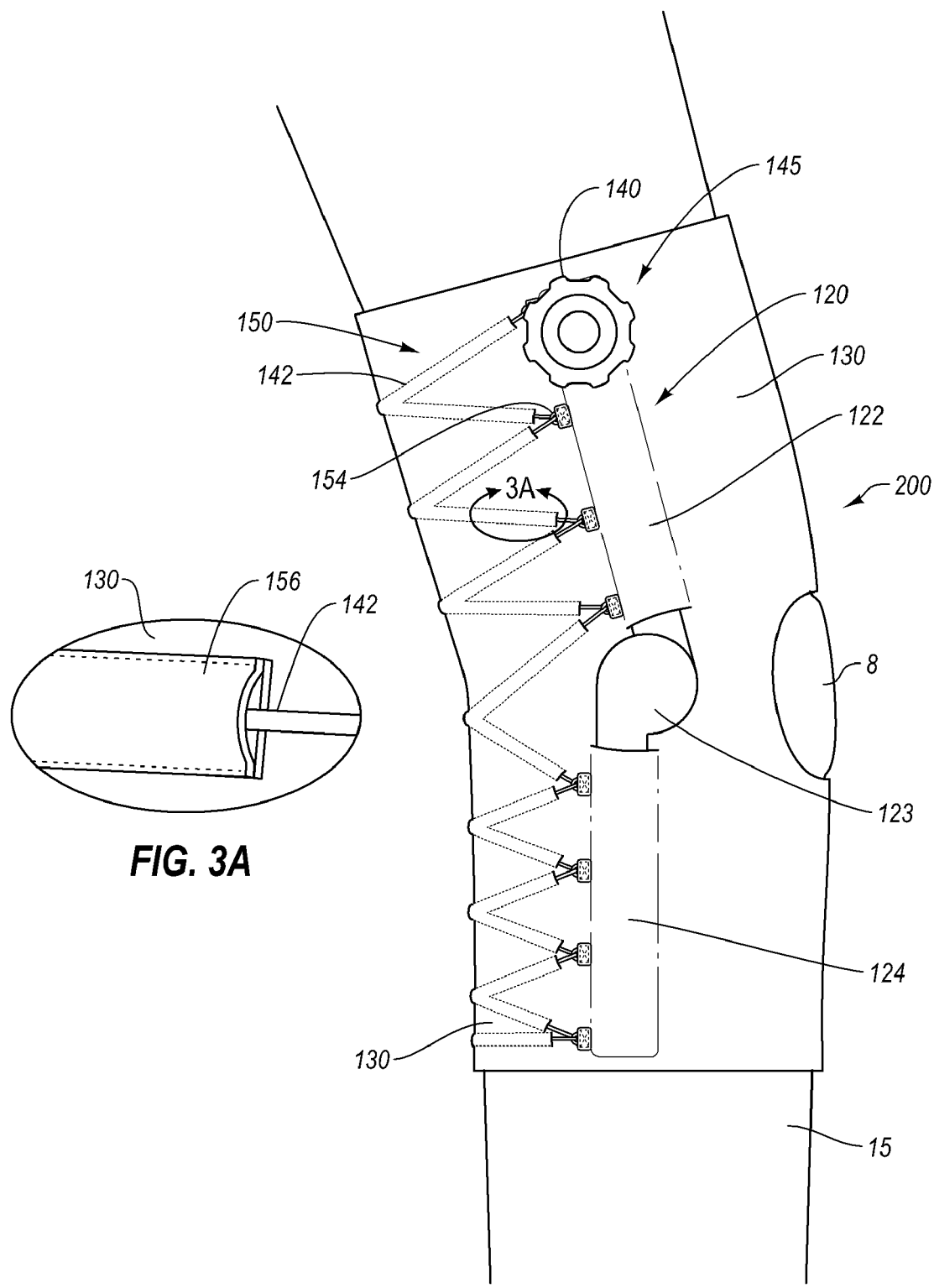
FIG. 3 shows a side view of an alternate embodiment of a cable-based orthopedic bracing system.
FIG. 3A shows an exploded, cut-away view of FIG. 3 of the area where the cable is positioned on the body material.

FIG. 3 shows a side view of an alternate embodiment of a cable-based orthopedic bracing system 200. As shown, the cable-based knee brace 200 comprises a frame 120, a body material 130, and an adjustment system 145. With the brace 200, the frame 120 has four parts: an upper and lower section 122 and 124 on each side of the knee 8. Further, with brace 200, the body material 130 is flexible and is typically neoprene. Lastly, the adjustment system 145 comprises an adjustment mechanism 140, a cable 142, and a routing system 150, which itself comprises eyelets 154 for guiding the cable 142 around the frame 120, and a sheath 156.

Thus, as with brace 100, the neoprene material 130 gives body to brace 200 while the frame 120 provides needed support to the knee 8. The brace 200 is placed over the knee 8 as one would put on a sock and then one adjusts the fit or tightness level with the aid of the adjustment system 145, which works in the same manner as does the adjustment system 45 of brace 100. Instead of the cable 142 being positioned primarily over the front portion of the brace 100, however, the cable 142 is positioned primarily over the rear portion of brace 200.

As shown in FIG. 3, the routing system 150 comprises eyelets 154, which are affixed to the rear side of each portion 122 and 124 of the frame 120. The cable 142 extends from the adjustment mechanism 140 and through the eyelets 154 and uniformly around the rear portion of the brace 200 and back to the adjustment mechanism 140. FIG. 3A shows an exploded, cut-away view of FIG. 3 of the area where the cable 142 is positioned on the body material 130. Specifically, FIG. 3A depicts the sheath 156, which protects the body material 130 and guides the cable 142 as it moves back and forth about the brace 200. Accordingly, the sheath 156 can be made of any suitable material to protect the body material 130 from wear and tear through use of the brace 200.

As the cable is tightened by the adjustment mechanism 140, it is pulled there and thereby pulled at each eyelet 154, thereby uniformly tightening the brace 200 to ensure a uniform, snug and proper fit around the user's knee 8. To loosen, the user need only loosen the ratchet system, i.e., the adjustment system 140, which thereby loosens the tension at each eyelet 154 location about the brace 200. Re-tightening can be achieved and re-loosening can be achieved in the same manner as it was originally performed. In this way, the cable-based knee brace 200 of the present invention is more comfortable, easier to use, simpler to loosen, simpler to tighten, and is longer lasting than conventional knee braces.

Figures 4, 4C:
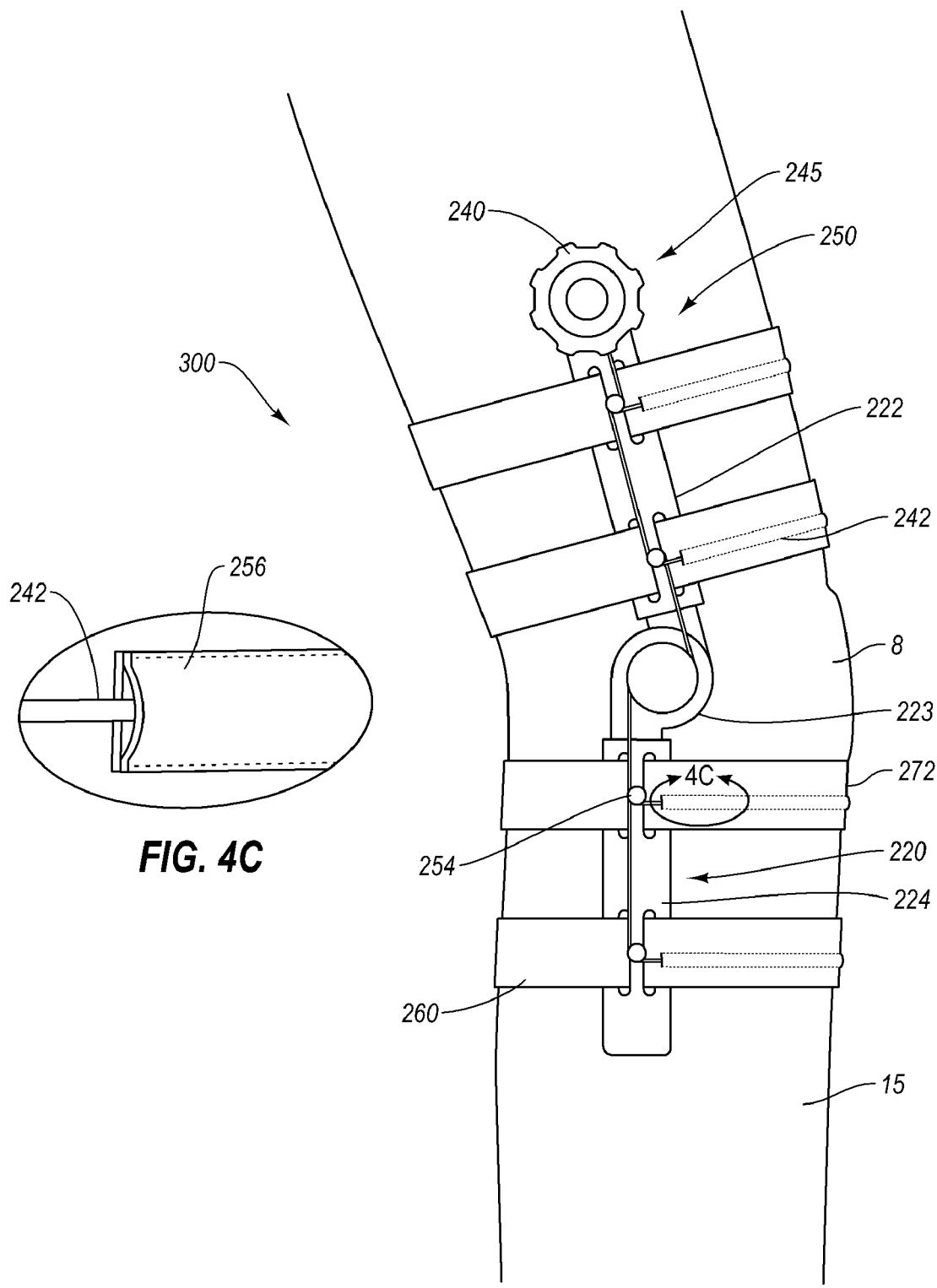
FIG. 4 shows a side view of an alternate embodiment of a cable-based orthopedic bracing system.
FIG. 4C shows an exploded, cut-away view of FIG. 4 of the area where the cable is positioned on the straps.

FIG. 4 shows a side view of an alternate embodiment of a cable-based orthopedic bracing system 300. As shown, the cable-based knee brace 300 comprises a frame 220 and an adjustment system 245. With the previous braces, the frame 220 has four parts: an upper 222 and lower section 124 on each side of the knee 8. Further, the adjustment system 245 comprises an adjustment mechanism 240, a cable 242, and a routing system 250, which itself comprises eyelets 254 for guiding the cable 242 around the frame 220 and particularly tight turns, and a sheath 256.

As opposed to previous braces, brace 300 does not have body material, but comprises straps. In the rear of the brace 300, the portions of the frame 220 are connected by straps 260 which are similar to straps 60 of brace 100B. As with brace 100B, these straps 260 can be any straps than can be readily connected and disconnected. The front of brace 300, however, has a strap system 270 that comprises straps 272. Each strap 272 extends between each respective portion 222 and 224 of the frame 220 to provide a path for the routing system 250. With brace 300, straps 272 are affixed between respective portions of frame 220 and are not detachable as are straps 260.

As shown in FIG. 4, the routing system 250 comprises eyelets 254, which are affixed to the side of each portion 222 and 224 of the frame 220. The cable 242 extends from the adjustment mechanism 240 and through the eyelets 254 and uniformly around the front portion of the brace 300, over the straps 272 back to the adjustment mechanism 240. FIG. 4C shows an exploded, cut-away view of FIG. 4 of the area where the cable 242 is positioned on the straps 272. Specifically, FIG. 4C depicts the sheath 256, which protects the straps 272 and guides the cable 242 as it moves back and forth about the brace 300. Accordingly, the sheath 256 can be made of any suitable material to protect the straps 272 from wear and tear through use of the brace 300.

As the cable is tightened by the adjustment mechanism 240, it is pulled there and thereby pulled at each eyelet 254 and over the straps 272, thereby uniformly tightening the brace 300 to ensure a uniform, snug and proper fit around the user's knee 8. To loosen, the user need only loosen the ratchet system, i.e., the adjustment system 240, which thereby loosens the tension at each eyelet 254 location and the straps 272 about the brace 300. Re-tightening can be achieved and re-loosening can be achieved in the same manner as it was originally performed. In this way, the cable-based knee brace 300 of the present invention is more comfortable, easier to use, simpler to loosen, simpler to tighten, and is longer lasting than conventional knee braces.

Figure 4A:
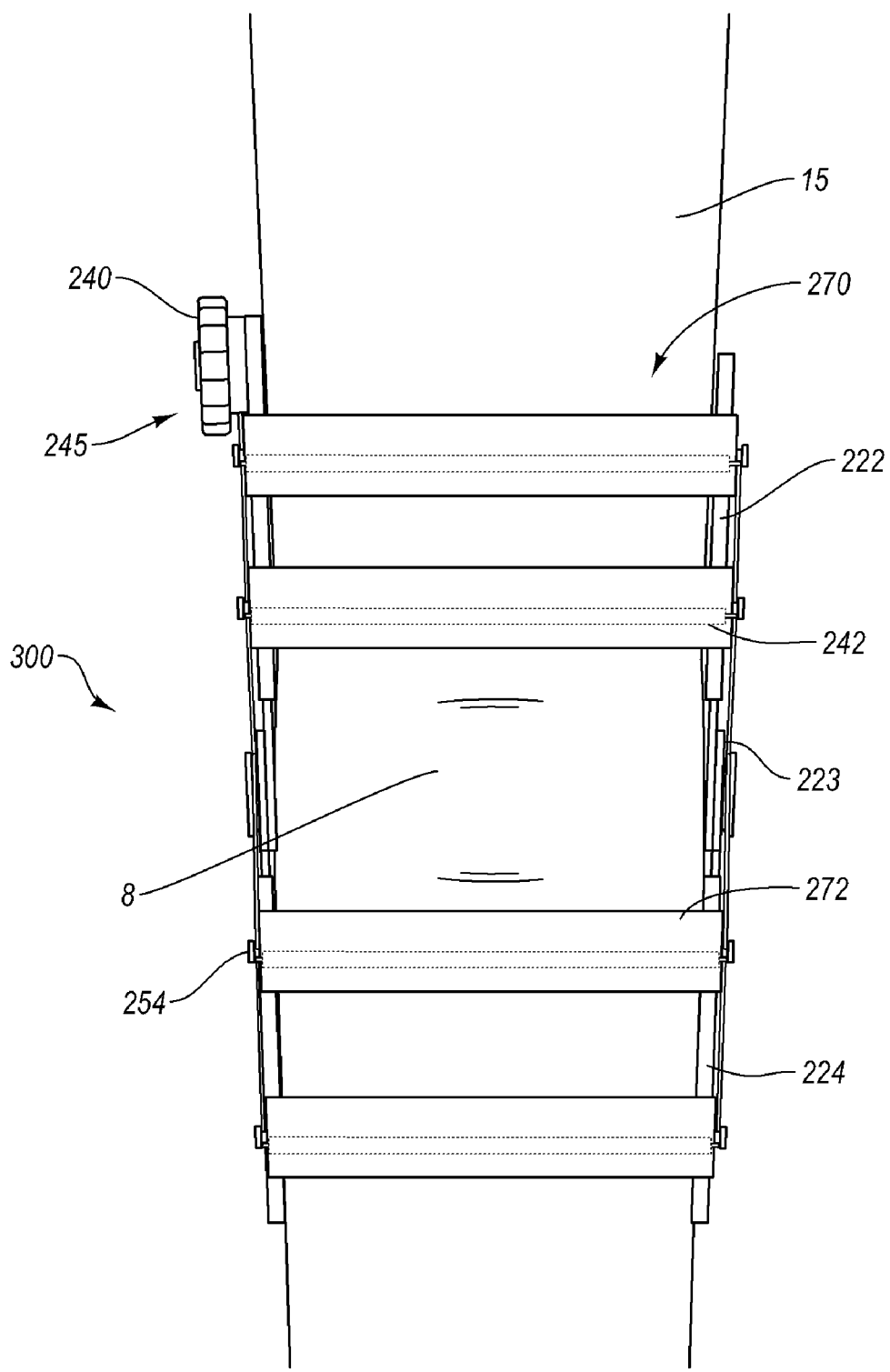
FIG. 4A shows a front view of the brace of FIG. 4.

FIG. 4A shows a front view of the brace 300 of the present invention. As shown in FIG. 4A, portions 222 and 224 of the frame 220 (including hinge 223) are visible from the front, as well as the adjustment mechanism 240, all of which are positioned on the side of the brace 300. Further, as shown, the adjustment system 245 is visible from the front, as it is positioned on the front of the brace 300 on frame 220 and the strap system 270.

Figure 4B:
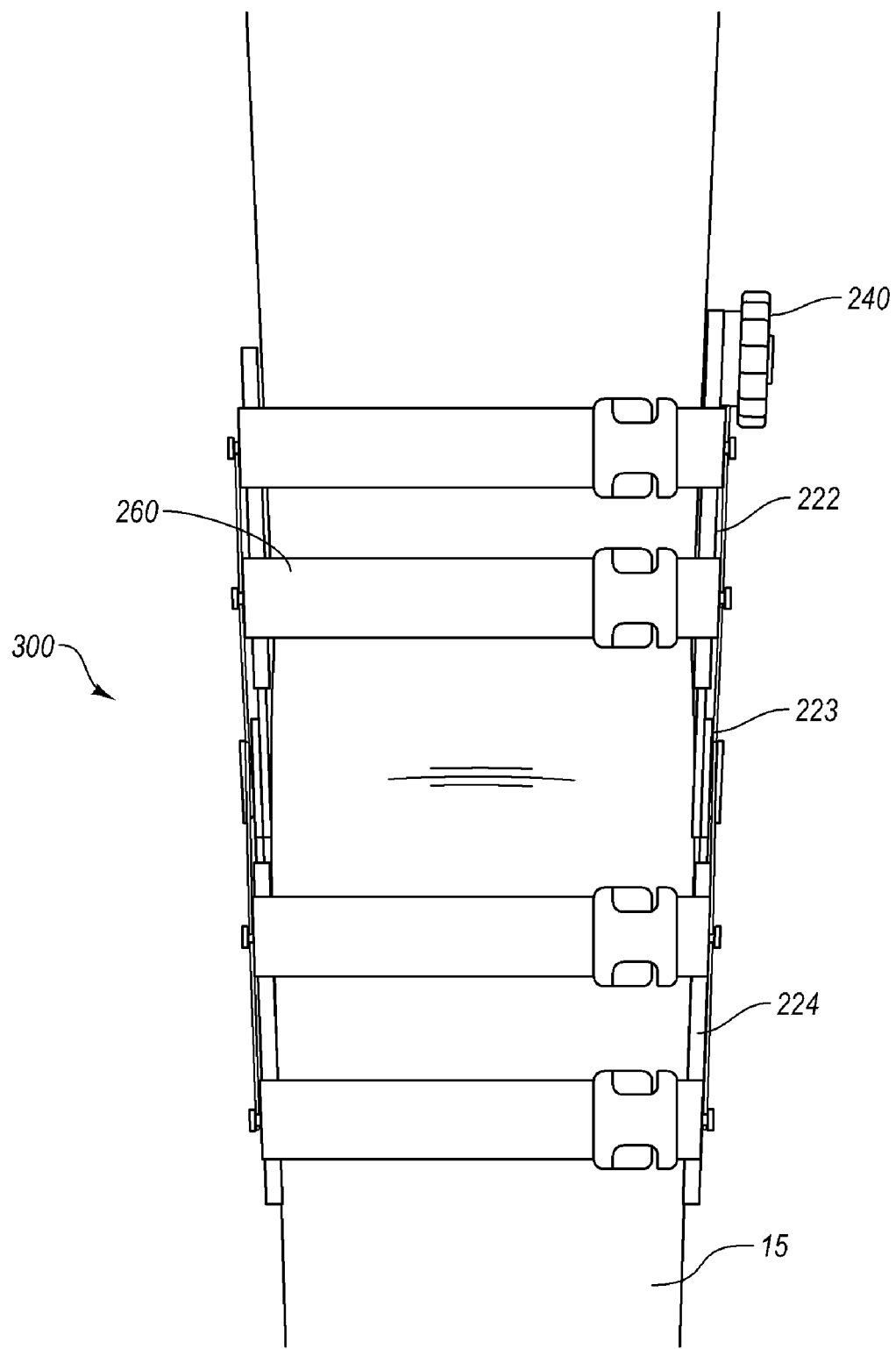
FIG. 4B shows a rear view of the brace of FIG. 4.

FIG. 4B shows a rear view of the brace 300 of the present invention. As shown in FIG. 4B, portions 222 and 224 of the frame 220 (including hinge 223) are visible from the rear, as well as the adjustment mechanism 240, all of which are positioned on the side of the brace 300. Further, as shown in FIG. 4B, the straps 260 are visible. With brace 300, it is by means of straps 260 that the user places the brace 300 on the knee 8 and removes the brace 300 from the knee 8.

Figure 5:
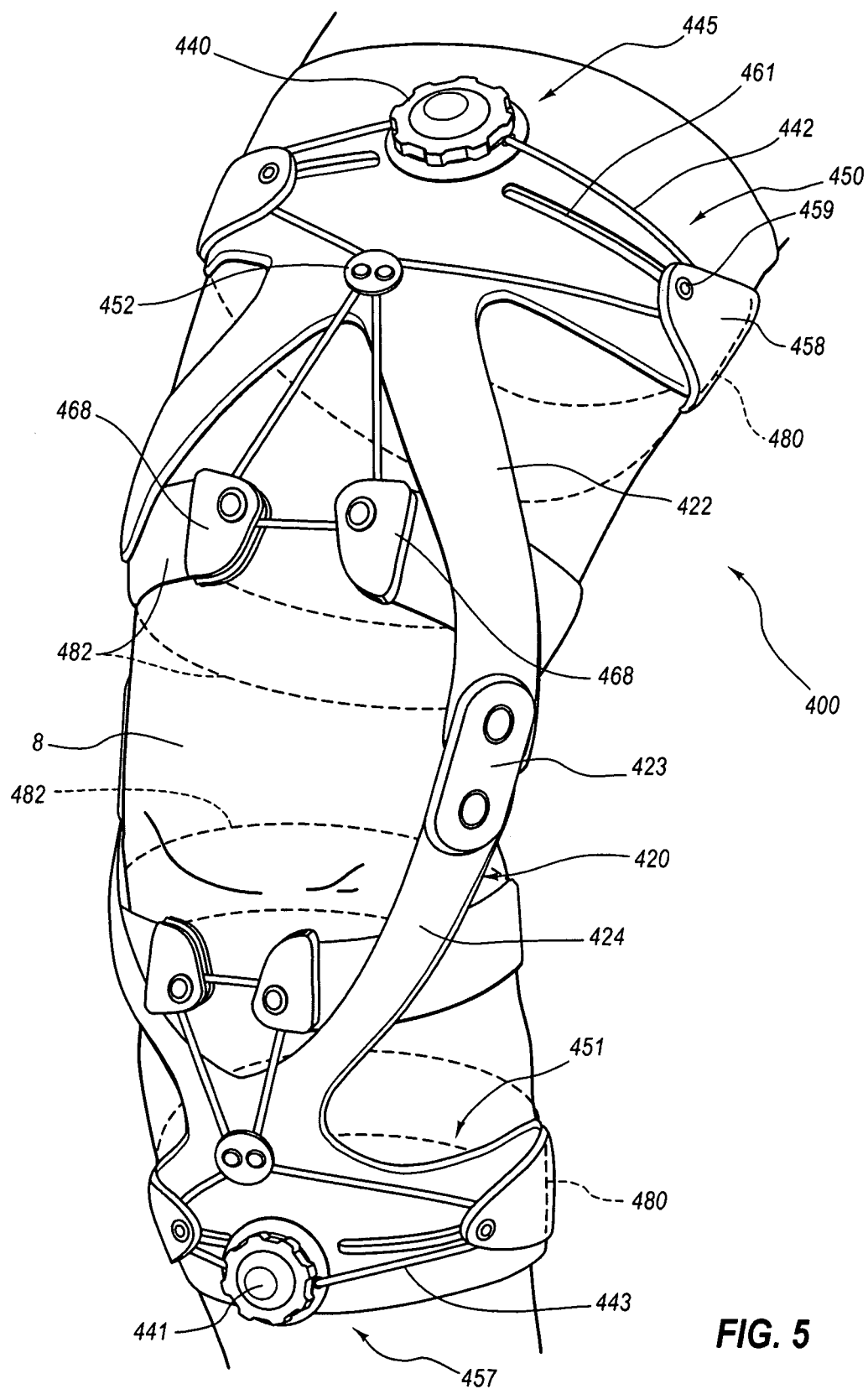
FIG. 5 shows a front view of an alternate embodiment of a cable-based orthopedic bracing system.

FIG. 5 shows a front view of an alternate embodiment of a cable-based orthopedic bracing system 400. As shown, the cable-based knee brace 400 comprises a frame 420 and two separate adjustment systems 445 and 457. Different from the previous braces, the frame 420 has two parts: an upper section 422 and a lower section 424, above and below the knee 8, respectively. The upper section 422 and lower section 424 are substantially mirror images of each other, operate in the same manner, and are rotatably connected to each other at hinge 423. On the upper section 422, the adjustment system 445 comprises an adjustment mechanism 440, a cable 442, and a routing system 450. With brace 400, the routing system 450 comprises an eyelet 452 for guiding the cable 442 around the frame 420 and particularly tight turns, and anchor clips 458 and 468.

Figure 5A:
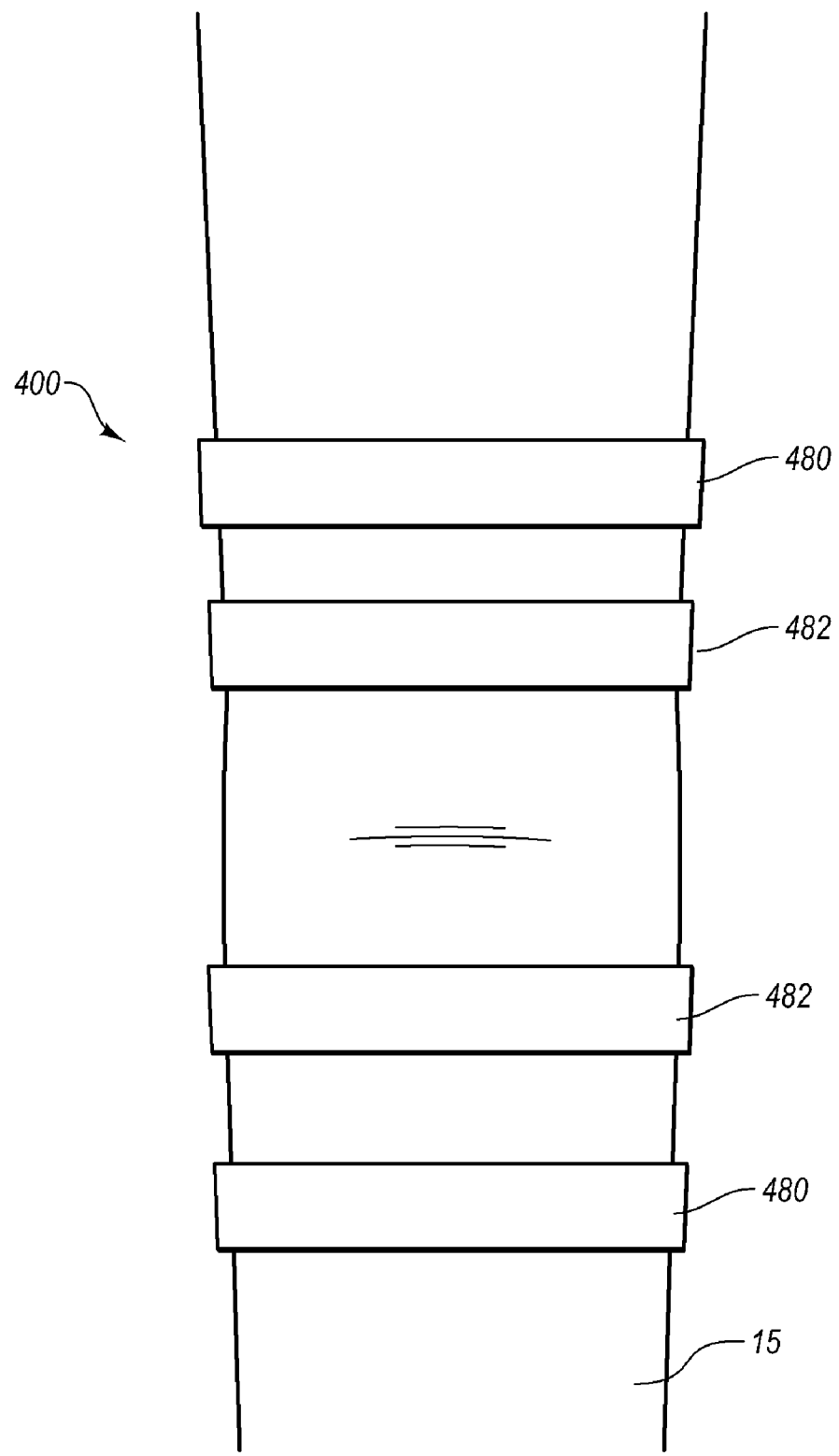
FIG. 5A shows a rear view of the brace of FIG. 5.

As with brace 300, brace 400 comprises straps. There are two straps 480 on the top and bottom of the brace 400 and two straps 482 in the middle of the brace 400. With brace 400, these straps 480 and 482 are not disconnected, but made of a flexible material such as flexible nylon. Accordingly, the brace 400 is placed over the knee 8 as one would put on a sock and then one adjusts the fit or tightness level with the aid of the adjustment system 445. Further, to aid in proper fit, the frame 420 of the brace 400 is customized or molded specially to fit each person's knee 8. FIG. 5A shows a rear view of the brace 400 of the present invention. As shown in FIG. 5A, straps 480 and 482 are visible from the rear.

As shown in FIG. 5 and as set forth above, the routing system 450 comprises an eyelet 452 for guiding the cable 442 around the frame 420 and particularly tight turns, and anchor clips 458 and 468. Each strap 480 is connected to the frame 420 by means of two anchor clips 458 located at the respective top 422 and bottom 424 frame portions. Each strap 482 is interconnected to the frame 420 by means of the two anchor clips 468 affixed to each strap 482.

The routing system 450 operates as follows. On each side of portion 422, the cable 442 extends from the adjustment mechanism 440, through one anchor clip 458, through eyelet 452 in the center of the frame portion 422, through eyelet 452 on the side of the frame portion 422, to a strap clip 474 on strap 482. As the cable 442 is tightened by the adjustment mechanism 440, it is pulled there and thereby pulled at and through each eyelet 452 and each anchor clip 458. Each eyelet 452 is affixed to the frame 420, but each anchor clip 458 is not affixed to the frame 420. The frame 420 has a groove 461 in which an anchor pin 459 rides back and forth as the cable 442 is tightened or loosened. Accordingly, during tightening, the pins 459 (which are connected to each anchor clip 458) move toward each other, and thereby pull the anchor clips 458 toward each other as viewed in FIG. 5, thereby tightening strap 480. Similarly, as the cable 442 is tightened, strap clips 474 (which are affixed to straps 482) move closer to each other, and thereby tighten strap 482. The adjustment system 457 on the lower portion 424 of the frame 420 operates in the same manner as does the adjustment system on the upper portion 422 of the frame. Accordingly, the adjustment system 457 comprises a separate routing system 451, a separate cable 443, and a separate adjustment mechanism 441.

The eyelet 452 is affixed to the frame 420, but each anchor clip 458 and 468 is not affixed to the frame 420. With respect to strap 480 and associated anchor clips 458, the frame 420 has a groove 461 in which an anchor pin 459 rides back and forth as the cable 442 is tightened or loosened. Accordingly, during tightening, the pins 459 (which are connected to each anchor clip 458) move toward each other, and thereby pull the anchor clips 458 toward each other as viewed in FIG. 5, thereby tightening strap 480. Similarly, as the cable 442 is tightened, anchor clips 468 (which are affixed to straps 482) move closer to each other, and thereby tighten strap 482. The adjustment system 457 on the lower portion 424 of the frame 420 operates in the same manner as does the adjustment system on the upper portion 422 of the frame. Accordingly, the adjustment system 457 comprises a separate routing system 451 and a separate adjustment mechanism 442.

Re-tightening can be achieved and re-loosening can be achieved in the same manner as it was originally performed. In this way, the cable-based knee brace 400 of the present invention is more comfortable, easier to use, simpler to loosen, simpler to tighten, and is longer lasting than conventional knee braces. In addition, because of the design of brace 400 and in particular, the manner in which the straps 480 and 482 are interconnected to the frame 420, the brace 400 has an additional benefit in that it eliminates the problem of "bunching" (i.e., gathering of excess material) of the straps 480 and 482 of the brace 400 as one tightens the brace 400 to properly fit it to one's knee 8.

Another aspect of the present invention is that it is advantageous in some embodiments and applications to have a cable to be positioned over a ligament of a joint. For example, it is particularly advantageous to have a cable or cables to be positioned over a ligament of an ankle because not only does the cable-based orthopedic bracing system of the present invention provide the improved support and benefits of the invention, but the cable positioned over ligaments would serve the purpose of conventional taping that a medical professional performs or places on or over ligaments of an ankle that needs such support. Thus, with any of the embodiments of the bracing system of the present invention where it is used to support an ankle, the cable may be situated or positioned over at least one ligament.

Although multiple embodiments of the invention are described herein in detail, it will be understood by those skilled in the art that variations may be made thereto without departing from the spirit of the invention or the scope of the claims. For example, the orthopedic bracing system of the present invention is not limited to knee braces, but is applicable to any bracing system on the body, such as an elbow brace or wrist brace. Further, the present invention also is applicable to areas other than orthopedic arena such as protective gear and sports padding. For example, one can apply the principles of the present invention to, e.g., football pads and arrive at football pads according to the present invention that can be tightened more easily and more readily and more uniformly than can be achieved with conventional football pads.

We claim:

1. An orthopedic bracing system for providing support to a joint connecting a first part of an individual's body to a second part of the individual's body, the bracing system comprising:

a frame configured to conform to the individual's body and configured to contact the individual to provide support to the joint, said frame having at least a first portion configured to connect to the first part of the individual's body, and a second portion configured to connect to the second part of the individual's body;

a first strap operatively associated with said frame, said first strap having a first terminal end, a second terminal end, and a length extending therebetween, said length of said first strap being adapted to at least partially surround a portion of the first part of the individual's body to facilitate securement of the first part of the individual's body to said first portion of said frame, and said first terminal end and second terminal end of said first strap being positioned on top of said first portion of said frame;

a second strap operatively associated with said frame, said second strap being adapted to circumferentially surround a portion of the first part of the individual's body to facilitate securement of the first part of the individual's body to said first portion of said frame, said second strap being positioned below said first portion of said frame;

a first cable linked directly to said first terminal end of said first strap and said second terminal end of said first strap, said first cable being interconnected to said first portion of said frame;

a third strap operatively associated with said frame, said third strap adapted to at least partially surround the second part of the individual's body to facilitate securement of the second part of the individual's body to a second portion of said frame;

a second cable linked to said third strap, said second cable being interconnected to said second portion of said frame; and an adjustment mechanism adapted to adjust the tightness level of said first cable independent of said second cable, said adjustment mechanism being adapted to draw said first terminal end of said first strap toward said second terminal end of said first strap, and tighten said second strap about the first part of the individual's body, thereby adjusting the fit of said first strap independent of the fit of said third strap.

2. The orthopedic bracing system of claim 1, further comprising: an eyelet affixed to said frame, wherein said eyelet guides a first section of said first cable about a first turn and a second portion of said first cable about a second turn, thereby preventing said first cable from overlapping itself.

3. The orthopedic bracing system of claim 1, wherein said frame further comprises at least two rigid members.

4. The orthopedic bracing system of claim 3, wherein said frame further comprises at least one hinge.

5. The orthopedic bracing system of claim 1, further comprising a groove extending through said frame.

6. The orthopedic bracing system of claim 5, further comprising an anchor pin, wherein said anchor pin is movably secured within said groove of said frame, and said first cable is routed about said anchor pin.

7. The orthopedic bracing system of claim 6, wherein said first strap is connected to said frame via said anchor pin.

8. The orthopedic bracing system of claim 1, wherein said adjustment mechanism comprises a ratchet.

9. The orthopedic bracing system of claim 1, further comprising eyelets affixed to said frame for guiding said first cable about said frame.

10. The orthopedic bracing system of claim 1, further comprising a second adjustment mechanism adapted to adjust the tightness level of said second cable independent of said first cable, thereby adjusting the fit of said third strap independent of the fit of the first strap.

11. An orthopedic bracing system for providing support to a joint of an individual, the bracing system comprising:
   a frame configured to conform to the individual's body and configured to contact at least a first portion of the individual's body on a first side of the joint and at least a second portion of the individual's body on an opposing second side of the joint to thereby provide support to the joint, said frame having first and second rigid members, said first rigid member including a central body portion, a first elongated portion extending downwardly away from said central body portion in a first direction and connecting to said second rigid member at a first hinge, and a second elongated portion extending downwardly away from said central body portion in a second direction and connecting to said second rigid member at a second hinge, whereby said first elongated portion and said second elongated portion are separated by a space therebetween;
   a first cable interconnected to said first rigid member of said frame, wherein said first cable extends into said space therebetween said first elongated portion and said second elongated portion, wherein the tightness level of said first cable influences the fit of the bracing system to the first portion of the individual's body; and
   a second cable interconnected to said second rigid member of said frame, wherein the tightness level of said second cable influences the fit of the bracing system to the second portion of the individual's body,
   wherein the tightness level of said first cable can be can be adjusted independent of the tightness level of said second cable thereby enabling the fit of the bracing system to the first portion of the individual's body and the fit of the bracing system to the second portion of the individual's body to be adjusted independently.

12. The orthopedic bracing system of claim 11, further comprising: an eyelet affixed to said frame, wherein said eyelet guides a first section of said first cable about a first turn and a second portion of said first cable about a second turn, thereby preventing said first cable from overlapping itself.

13. The orthopedic bracing system of claim 11, wherein said second rigid member includes a second central body portion, a third elongated portion extending upwardly away from said second central body portion in a third direction and connecting to said first rigid member at said first hinge, and a fourth elongated portion extending upwardly away from said second central body portion in a fourth direction and connecting to said first rigid member at said second hinge, whereby said third elongated portion and said fourth elongated portion are separated by a space therebetween.

14. The orthopedic bracing system of claim 11, wherein said body material is neoprene.

15. The orthopedic bracing system of claim 11, further comprising a first adjustment mechanism adapted to adjust the tightness level of said first cable.

16. The orthopedic bracing system of claim 11, further comprising a groove extending through said frame.

17. The orthopedic bracing system of claim 16, further comprising an anchor pin, wherein said anchor pin is movably secured within said groove of said frame, said first cable is routed about said anchor pin.

18. The orthopedic bracing system of claim 11, further comprising eyelets affixed to said frame for guiding said first cable about said frame.

19. An orthopedic bracing system for providing support to a joint of an individual, the bracing system comprising:
   a frame configured to conform to the individual's body and configured to contact the individual to provide support to the joint, said frame having a first rigid portion pivotally connected to a second rigid portion;
   a first strap having first and second ends interconnected to said first rigid portion of said frame;
   a first cable interconnected to said first rigid portion of said frame and said first strap;
   an eyelet affixed to said frame, wherein said eyelet guides a first section of said first cable about a first turn and a second portion of said first cable about a second turn, thereby preventing said first cable from overlapping itself;
   a second cable interconnected to said second rigid portion of said frame;
   a first adjustment mechanism adapted to adjust the tightness level of said first cable independent of said second cable, thereby adjusting the fit of a portion of the bracing system associated with said first rigid portion by pulling said first and second ends of said first strap over and along said first rigid portion of said frame toward each other; and
   a second adjustment mechanism adapted to adjust the tightness level of said second cable independent of said first cable, thereby adjusting the fit of the portion of the bracing system associated with said second rigid portion independent of the fit of the portion of the bracing system associated with said first rigid portion.

20. The orthopedic bracing system of claim 19, further comprising a groove extending in said frame.

21. The orthopedic bracing system of claim 20, further comprising an anchor pin, wherein said anchor pin is movably secured within said groove of said frame, and said first cable is routed about said anchor pin.

22. The orthopedic bracing system of claim 21, wherein said first strap is connected to said frame via said anchor pin.

23. The orthopedic bracing system of claim 19, wherein said frame further comprises at least one hinge.

24. The orthopedic bracing system of claim 19, wherein at least said first adjustment mechanism comprises a ratchet.

25. The orthopedic bracing system of claim 19, further comprising one or more additional eyelets affixed to said frame for guiding said second cable about said frame.

26. The orthopedic bracing system of claim 20, wherein said one or more additional eyelets guides a first section of said second cable about a first turn and a second portion of said second cable about a second turn, thereby preventing said second cable from overlapping itself.

27. An orthopedic bracing system for providing support to a joint of an individual, the bracing system comprising:
a frame configured to conform to the individual's body and configured to contact the individual such that it can provide support to the joint, said frame having two portions configured to connect to a first part of the individual's body and to a second part of the individual's body, said frame including a groove extending through a portion thereof;
at least a first strap interconnected to said frame by an anchor pin, wherein said anchor pin is movably secured within said groove of said frame;
a cable interconnected to said frame and routed about said anchor pin; and
an adjustment mechanism adapted to adjust the tightness level of said cable thereby causing said anchor pin to move within said groove, wherein movement of said anchor pin within said groove adjusts the tightness of said at least first strap.

28. The orthopedic bracing system of claim 27, wherein said frame further comprises at least two rigid members.

29. The orthopedic bracing system of claim 27, wherein said frame further comprises at least one hinge.

30. The orthopedic bracing system of claim 27, further comprising eyelets affixed to said frame for guiding said cable about said frame.

31. The orthopedic bracing system of claim 27, wherein said at least one strap is made of flexible material.

32. The orthopedic bracing system of claim 27, further comprising an anchor clip that houses said anchor pin.

33. The orthopedic bracing system of claim 27, further comprising at least two anchor clips, wherein said at least one strap is affixed to and between said at least two anchor clips.

34. The orthopedic bracing system of claim 27, further comprising at least one second strap interconnected to said frame by means of at least one strap clip, wherein said at least one strap clip is affixed to said cable.

35. The orthopedic bracing system of claim 27, wherein said frame has been customized to fit the body parts of a particular individual.

36. An orthopedic bracing system for providing support to a joint of an individual, the bracing system comprising:
a frame configured to conform to the individual's body and configured to contact the individual to provide support to the joint, said frame having at least a first portion configured to connect to a first part of an individual's body, and a second portion configured to connect to a second part of the individual's body, said first portion including:
a central body portion, said central body portion having first and second grooves,
a first elongated portion extending downwardly away from said first central body portion in a first direction, and
a second elongated portion extending downwardly away from said first central body portion in a second direction, whereby said first elongated portion and said second elongated portion are separated by a space therebetween;
a first strap having a first end, a second end, and a length extending between said ends, said length of said first strap being positioned to wrap about a first portion of the individual's body, said first end of said first strap being secured over said central body portion to a first anchor pin within said first groove, and said second end of said first strap being secured over said central body portion to a second anchor pin within said second groove;
a second strap having a first end and a second end, said second strap being adapted to circumferentially surround a portion of an individual's body, said first end of said second strap having a first anchor clip secured thereto and said second end of said second strap having a second anchor clip secured thereto;
an adjustment mechanism secured to said central body portion between said first groove and said second groove;
an eyelet affixed to said central body portion below said adjustment mechanism;
a cable extending from a first side of said adjustment mechanism to said first anchor pin, about said first anchor pin to said eyelet, about said eyelet to said first anchor clip, about said first anchor clip to said second anchor clip, about said second anchor clip to said eyelet, about said eyelet to said second anchor pin, about said second anchor pin and into a second side of said adjustment mechanism;
wherein said eyelet guides a first section of said cable about a first turn and a second portion of said cable about a second turn, thereby preventing said first cable from overlapping itself; and
wherein said adjustment mechanism is adapted to adjust the tightness level of said cable thereby adjusting the fit of the bracing system.

* * * * *

UNITED STATES PATENT AND TRADEMARK OFFICE
CERTIFICATE OF CORRECTION

PATENT NO. : 7,806,842 B2  
APPLICATION NO. : 11/697685  
DATED : October 5, 2010  
INVENTOR(S) : Stevenson et al.

Page 1 of 1

It is certified that error appears in the above-identified patent and that said Letters Patent is hereby corrected as shown below:

In the Specification

Column 2  
Line 5, change "one a hinge" to --one hinge--  
Line 45, change "shows front" to --shows a front--

Column 3  
Line 51, change "frame 40" to --frame 20--

Column 7  
Line 7, change "strap clip 474" to --strap clip 468--  
Line 19, change "474 (which" to --468 (which--  
Line 35, change "anchor" to --strap--  
Line 41, change "mechanism 442" to --mechanism 441--

Signed and Sealed this  
Second Day of June, 2015

Michelle K. Lee  
*Director of the United States Patent and Trademark Office*